United States Patent
Keating et al.

(10) Patent No.: US 12,419,625 B2
(45) Date of Patent: Sep. 23, 2025

(54) DEVICES FOR DYNAMIC SIZING AND SAGITTAL BALANCING IN TOTAL KNEE ARTHROPLASTY

(71) Applicant: OMICRON ORTHOPEDIC TECHNOLOGY, LLC, Chicago, IL (US)

(72) Inventors: Timothy Chandler Keating, Chicago, IL (US); Arthur William Keating, Efland, NC (US)

(73) Assignee: OMICRON ORTHOPEDIC TECHNOLOGY, LLC, Chicago, IL (US)

( * ) Notice: Subject to any disclaimer, the term of this patent is extended or adjusted under 35 U.S.C. 154(b) by 396 days.

(21) Appl. No.: 17/907,495

(22) PCT Filed: Apr. 21, 2021

(86) PCT No.: PCT/US2021/028345
§ 371 (c)(1),
(2) Date: Sep. 27, 2022

(87) PCT Pub. No.: WO2021/216672
PCT Pub. Date: Oct. 28, 2021

(65) Prior Publication Data
US 2023/0117580 A1   Apr. 20, 2023

Related U.S. Application Data

(60) Provisional application No. 63/014,895, filed on Apr. 24, 2020.

(51) Int. Cl.
*A61B 17/02* (2006.01)
*A61B 17/00* (2006.01)

(52) U.S. Cl.
CPC .. *A61B 17/025* (2013.01); *A61B 2017/00367* (2013.01); *A61B 2017/0268* (2013.01)

(58) Field of Classification Search
CPC .......... A61B 17/025; A61B 2017/0268; A61B 2017/00367; A61F 2/4657;
(Continued)

(56) References Cited

U.S. PATENT DOCUMENTS 6,022,377 A    2/2000 Nuelle et al.
2002/0156480 A1*  10/2002 Overes ................. A61B 17/025
606/90
(Continued)

OTHER PUBLICATIONS

International Search Report dated Aug. 13, 2021 in International Patent Application No. PCT/US2021/028345.
(Continued)

*Primary Examiner* — Samuel S Hanna
(74) *Attorney, Agent, or Firm* — McDonnell Boehnen Hulbert & Berghoff LLP

(57) ABSTRACT

The present disclosure describes one or more embodiment of devices for assisting femoral component placement in total knee arthroplasty. The device may include a distractor configured to provide a constant distracting force. The distractor may include a main body of the distractor, a tibial paddle fixedly connected to the main body, the tibial paddle configured to engage a top of a tibia, at least one femoral paddle configured to push against a bottom of a femur, a spring housing fixed on the main body of the distractor, and a coiled constant force spring disposed in the spring housing. The spring housing is attached to an outer end of the coiled constant force spring, and the coiled constant force spring is configured to apply the constant distracting force on the at least one femoral paddle. The device further includes a mechanical apparatus for locating an isometric point of the femur.

11 Claims, 18 Drawing Sheets

(58) Field of Classification Search
CPC ...... A61F 2002/4658; A61F 2002/4661; A61F 2002/4668
See application file for complete search history.

(56) References Cited

U.S. PATENT DOCUMENTS

2010/0100102 A1    4/2010  Duggineni et al.
2012/0238911 A1    9/2012  Chessar et al.
2014/0288563 A1    9/2014  Claypool et al.

OTHER PUBLICATIONS

Written Opinion of the International Searching Authority dated Aug. 13, 2021 in International Patent Application No. PCT/US2021/028345.

* cited by examiner

DEVICES FOR DYNAMIC SIZING AND SAGITTAL BALANCING IN TOTAL KNEE ARTHROPLASTY

RELATED APPLICATION

This application is a 371 U.S. national phase of PCT/US2021/028345, filed Apr. 21, 2021, which claims the benefit of priority to U.S. Provisional Application No. 63/014,895 entitled "Devices for Dynamic Sizing and Sagittal Balancing in Total Knee Arthroplasty," filed on Apr. 24, 2020, the contents of both applications which are hereby incorporated by reference in their entirety.

FIELD OF THE TECHNOLOGY

The present disclosure relates to a device used in a total knee arthroplasty, and is particularly directed to a device for assisting femoral component placement in total knee arthroplasty.

BACKGROUND

Joint replacement surgery, for example, total knee arthroplasty, may be performed on patients with certain joint diseases. Some existing methods in femoral component placement utilize either "measured resection" or "gap balancing" to achieve a knee that has equal and rectangular gaps between the femur and tibia with the knee at full extension, and/or 90 degrees of flexion. Some issues/problems may arise for some existing methods with traditional thinking that a knee is perfectly "balanced" as long as these two conditions are met. For example, a perfect sagittal balance in total knee arthroplasty may occur when the isometric point of the femoral implant overlaps with the isometric point of the native knee; and this may allow the knee to be consistently stable to varus and valgus force at full extension, mid flexion, and deep flexion and to promote comfort and function during activity. Another issue/problem may be that there is no device readily available with high efficiency and cost-effectiveness for dynamic sizing and sagittal balancing in total knee arthroplasty. Recently, robotic technology has evolved that can predict flexion and extension gaps prior to making bone cuts, but currently there is no mechanical instrumentation that allows a surgeon to assess dynamic balance prior to making bone cuts.

The present disclosure describes devices for assisting femoral component placement in total knee arthroplasty, which address at least one or more drawbacks discussed above.

BRIEF SUMMARY

Embodiments of the present disclosure include methods, devices, and computer readable medium for assisting femoral component placement in total knee arthroplasty.

In a first aspect, the present disclosure is directed to a device for assisting femoral component placement in total knee arthroplasty. The device may include a distractor configured to provide a constant distracting force. The distractor may include a main body of the distractor, a tibial paddle fixedly connected to the main body, the tibial paddle configured to engage a top of a tibia, at least one femoral paddle configured to push against a bottom of a femur, a spring housing fixed on the main body of the distractor, and a coiled constant force spring disposed in the spring housing, the spring housing attached to an outer end of the coiled constant force spring, the coiled constant force spring configured to apply the constant distracting force on the at least one femoral paddle.

In one example of the first aspect, the distractor further includes an inner gear attached to an inner end of the coiled constant force spring, and a primary rack fixedly connected to one of the at least one femoral paddle, the primary rack operatively connected with the inner gear, a rotation of the inner gear configured to slide the one of the at least one femoral paddle.

In another example of the first aspect, the distractor further includes a winding gear disposed on the main body of the distractor, the winding gear operatively connected to the spring housing, the winding gear rotatable in one direction configured to wind the coiled constant force spring.

In another example of the first aspect, the at least one femoral paddle comprises a first femoral paddle and a second femoral paddle, and the distractor further includes a first rack fixedly connected to the first femoral paddle, a second rack fixedly connected to the second femoral paddle, and one or more internal gears operatively connected with the first rack and the second rack.

In another example of the first aspect, a top surface of each of the at least one femoral paddle and a bottom surface of the tibial paddle are substantially parallel.

In another example of the first aspect, the device further includes a mechanical graph configured to locate an isometric point of the femur, wherein the mechanical graph comprises: a base fixedly connected to the tibial paddle of the distractor, a tower fixedly connected to the base, a longitudinal axis of the tower being substantially perpendicular to a plane of the base, the tower comprising a first column, a vertical marker slidable along the first column, a vertical reference slidable along the first column, the vertical reference comprising a slot, and a drive shaft assembly comprising a shaft and at least one shaft arm disposed between a distal portion and a proximal portion, the distal portion of the drive shaft assembly slidable along the tower, the distal portion of the drive shaft assembly operatively connected to the vertical reference, the proximal portion of the drive shaft assembly operatively connected to a femoral block.

In another example of the first aspect, the distal portion of the drive shaft assembly comprises: a distal baseplate disposed at a terminal of the distal portion, a rotating arm operatively connected with the shaft via a rack and pinion mechanism at the distal baseplate, and a cylindrical extension disposed at an end of the rotating arm, the cylindrical extension slidable in the slot of the vertical reference.

In another example of the first aspect, the proximal portion of the drive shaft assembly comprises: a link rotatably connected with a proximal end of the at least one shaft arm, a stationary gear fixedly connected to the link, and a mobile gear fixedly connected to the shaft, the mobile gear operatively engaged with the stationary gear.

In another example of the first aspect, a gear ratio between the stationary gear and the mobile gear is 1:1.

In another example of the first aspect, the device further includes a femoral block comprising: a main body of the femoral block comprising a set of holes configured for a set of fasteners to secure the femoral block to the femur, and a sliding member slidable relative to the main body, the sliding member comprising a gear operatively connected to a rack of the main body via a rack and pinion mechanism.

In another example of the first aspect, the sliding member comprises: a set of reference holes aligned with a set of slots in the main body, and a slot configured to receive a femoral sizer.

In another example of the first aspect, the link of the drive shaft assembly comprises a set of protruding portions operatively engaging with a set of grooves of the femoral block, and the link of the drive shaft assembly is configured to slide in the set of groove of the femoral block via a rack and pinion mechanism.

In a second aspect, the present disclosure describes another device for assisting femoral component placement in total knee arthroplasty. The device includes a mechanical graph configured to locate an isometric point of a femur. The mechanical graph may include a base, a tower fixedly connected to the base, a longitudinal axis of the tower being substantially perpendicular to a plane of the base, the tower comprising a first column, a vertical marker slidable along the first column, a vertical reference slidable along the first column, the vertical reference comprising a slot, and a drive shaft assembly comprising a shaft and at least one shaft arm disposed between a distal portion and a proximal portion, the distal portion of the drive shaft assembly slidable along the tower, the distal portion of the drive shaft assembly operatively connected to the vertical reference, the proximal portion of the drive shaft assembly operatively connected to a femoral block.

In one example of the second aspect, the distal portion of the drive shaft assembly comprises: a distal baseplate disposed at a terminal of the distal portion, a rotating arm operatively connected with the shaft via a rack and pinion mechanism at the distal baseplate, and a cylindrical extension disposed at an end of the rotating arm, the cylindrical extension slidable in the slot of the vertical reference.

In another example of the second aspect, the proximal portion of the drive shaft assembly comprises: a link rotatably connected with a proximal end of the at least one shaft arm, a stationary gear fixedly connected to the link, and a mobile gear fixedly connected to the shaft, the mobile gear operatively engaged with the stationary gear, wherein a gear ratio between the stationary gear and the mobile gear is 1:1.

In another example of the second aspect, the device further includes a distractor configured to provide a constant distracting force, wherein the distractor comprises: a main body of the distractor, a tibial paddle fixedly connected to the main body, the tibial paddle configured to engage a top of a tibia, the tibial paddle fixedly connected to the base of the mechanical graph, at least one femoral paddle configured to push against a bottom of the femur, wherein a top surface of each of the at least one femoral paddle and a bottom surface of the tibial paddle are substantially parallel, a spring housing fixed on the main body of the distractor, a coiled constant force spring disposed in the spring housing, the spring housing attached to an outer end of the coiled constant force spring, the coiled constant force spring configured to apply the constant distracting force on the at least one femoral paddle, an inner gear attached to an inner end of the coiled constant force spring, a primary rack fixedly connected to one of the at least one femoral paddle, the primary rack operatively connected with the inner gear, a rotation of the inner gear configured to slide the one of the at least one femoral paddle, and a winding gear disposed on the main body of the distractor, the winding gear operatively connected to the spring housing, the winding gear rotatable in one direction configured to wind the coiled constant force spring.

In another example of the second aspect, the at least one femoral paddle comprises a first femoral paddle and a second femoral paddle, and the distractor further comprises: a first rack fixedly connected to the first femoral paddle, a second rack fixedly connected to the second femoral paddle, and one or more internal gears operatively connected with the first rack and the second rack.

In another example of the second aspect, the device further includes a femoral block comprising: a main body of the femoral block comprising a set of holes configured for a set of fasteners to secure the femoral block to the femur, and a sliding member slidable relative to the main body, the sliding member comprising a gear operatively connected to a rack of the main body via a rack and pinion mechanism.

In another example of the second aspect, the sliding member comprises: a set of reference holes aligned with a set of slots in the main body, and a slot configured to receive a femoral sizer.

In another example of the second aspect, a link of the drive shaft assembly comprising a set of protruding portions operatively engaging with a set of grooves of the femoral block, and the link of the drive shaft assembly configured to slide in the set of groove of the femoral block via a rack and pinion mechanism.

The above and other aspects and their implementations are described in greater details in the drawings, the descriptions, and the claims.

BRIEF DESCRIPTION OF THE DRAWINGS

The system, device, product, and/or method described below may be better understood with reference to the following drawings and description of non-limiting and non-exhaustive embodiments. The components in the drawings are not necessarily to scale. Emphasis instead is placed upon illustrating the principles of the disclosure.

FIGS. 3A-3I are schematic diagrams of one embodiment of a mechanical graph.

Figure 1A:
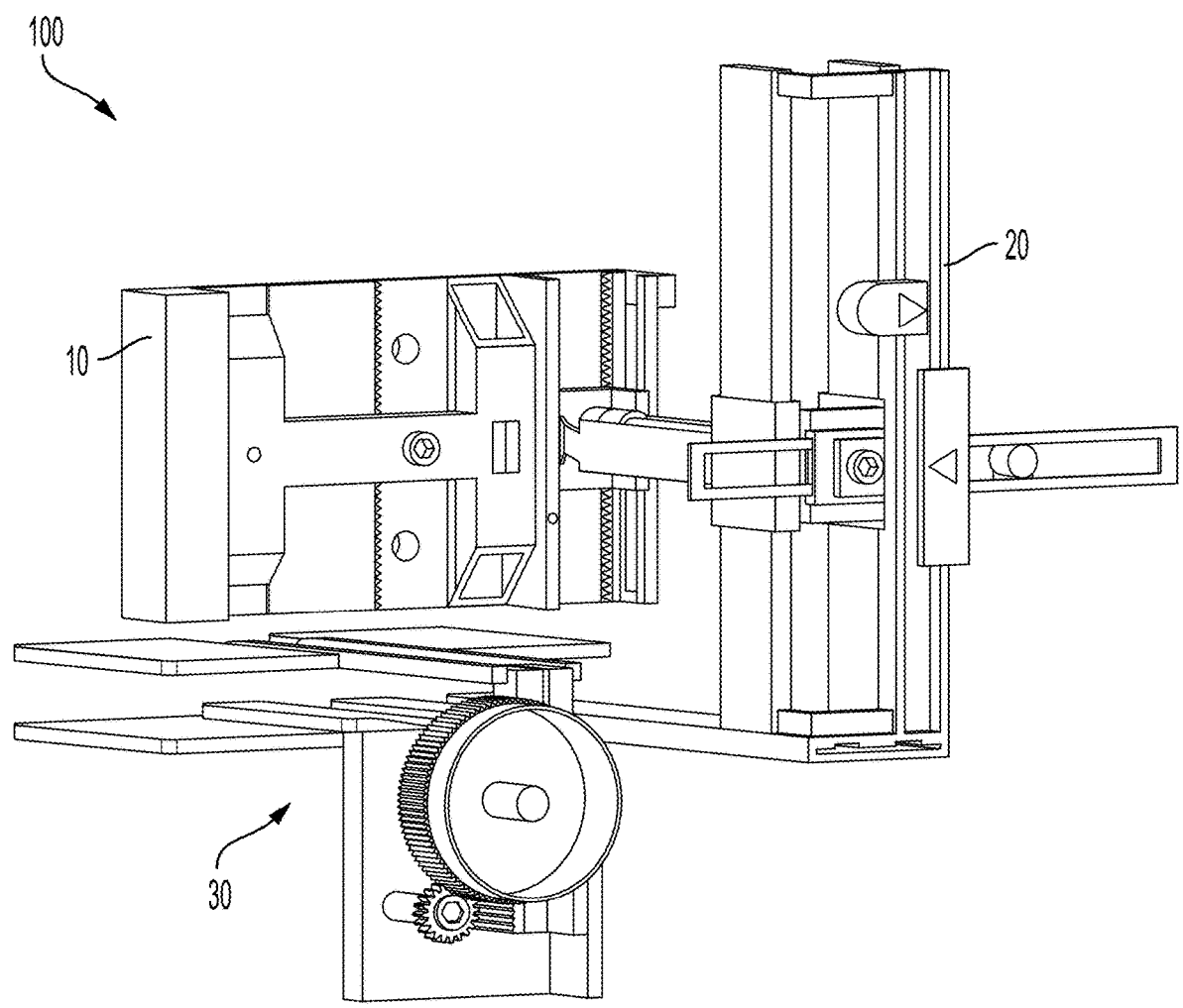
FIG. 1A is a schematic diagram of one embodiment of a device for assisting femoral component placement in total knee arthroplasty.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

The device and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the device and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Throughout the specification and claims, terms may have nuanced meanings suggested or implied in context beyond an explicitly stated meaning. Likewise, the phrase "in one embodiment" or "in one implementation" as used herein does not necessarily refer to the same embodiment or implementation and the phrase "in another embodiment" or "in another implementation" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

Unless defined otherwise, all technical and scientific terms used herein have the same meaning as commonly understood by one of skill in the art to which the invention pertains. Although any methods and materials similar to or equivalent to those described herein may be used in the practice or testing of the present invention, the preferred methods and materials are described herein.

The present disclosure describes devices for assisting femoral component placement in total knee arthroplasty, particularly for dynamic sizing and sagittal balancing in total knee arthroplasty. The present disclosure may address one or more the existing drawbacks by providing a constant force to tension soft tissues around the knee; acting as a mechanical graph to project the vertical displacement of a single point on the femur in the sagittal plane throughout every degree of flexion; and/or facilitating femoral component positioning through the placement of drill holes for placing standard femoral cutting guides.

Some existing technologies may use mechanical instrumentation to allow for assessment of a tibiofemoral joint space at limited flexion angles, for example, only at full extension and 90 degrees of flexion. This may confound the appropriate soft tissue tension at all other degrees of flexion in common knee pathologies for patients undergoing total knee arthroplasty. One such example of this pathology may be a patient with a preoperative flexion contracture, as tensioning the joint at full extension places tension on the posterior capsule, while vanes-valgus stability at all other degrees of flexion has a greater contribution from the collateral ligaments and remaining cruciate ligaments. There may be no commercially available mechanical technology for tensioning the joint space with a constant force to allow for the assessment of the femorotibial joint space at a full range of all degrees of flexion. There may be no commercially available mechanical technology functions on the concept of elucidating and re-creating the native isometry of the knee as a means to execute ideal sagittal balance. There may be one or more commercially available technology that depends on the placement of optical tracking arrays and hand-held robotics to predict joint-ligament balance.

The present disclosure describes embodiments to deliver similar accuracy more efficiently and cost-effectively, and with the opportunity to use with a wide range of implants in total knee arthroplasty.

The present disclosure describes embodiments to assess the need for soft tissue release in a knee undergoing total knee arthroplasty by measuring the femorotibial joint space at varying degrees of flexion under constant tension. The present disclosure may allow a medical care provider, for example, a surgeon, to recognize a flexion contracture due to a tight posterior capsule as the joint space will be more narrow in full extension and the first few degrees of flexion compared to mid flexion and 90 degrees of flexion when the tension is transferred to the collateral ligaments. A decreased femorotibial joint space at 90 degrees of extension compared to mid-flexion may also alert the medical care provider to the possibility of a tight posterior cruciate ligament (PCL) when performing a cruciate retaining total knee arthroplasty.

The present disclosure describes embodiments to determine an isometric point of the knee based on the use of a mechanical graph to project the vertical displacement of a single point on the femur through a whole range of motion. The isometric point of the native femur is a point on the femur that occupies a constant vertical displacement in relation to the tibia while the soft tissues are tensioned at a constant force. This tracking functionality of the present disclosure is modular and can be systematically assessed to quickly align that point to the isometric point of the femur.

The present disclosure describes embodiments to facilitate the accurate placement of the femoral component based on overlapping the isometric point of the femur with the isometric point of the implant. Overall, the present disclosure may allow reliable restoration of the native joint and the creation of a dynamic flexion gap that is equal through all degrees of flexion, ensuring the target sagittal position for a femoral component is reliably achieved.

The present disclosure describes embodiments of a stand-alone device available for use with a wide variety of instrumentation systems, and/or an add-on device to an implantation system. For example, the present disclosure may be incorporated into a variety of navigation applications in total knee arthroplasty (TKA).

Figure 1B:
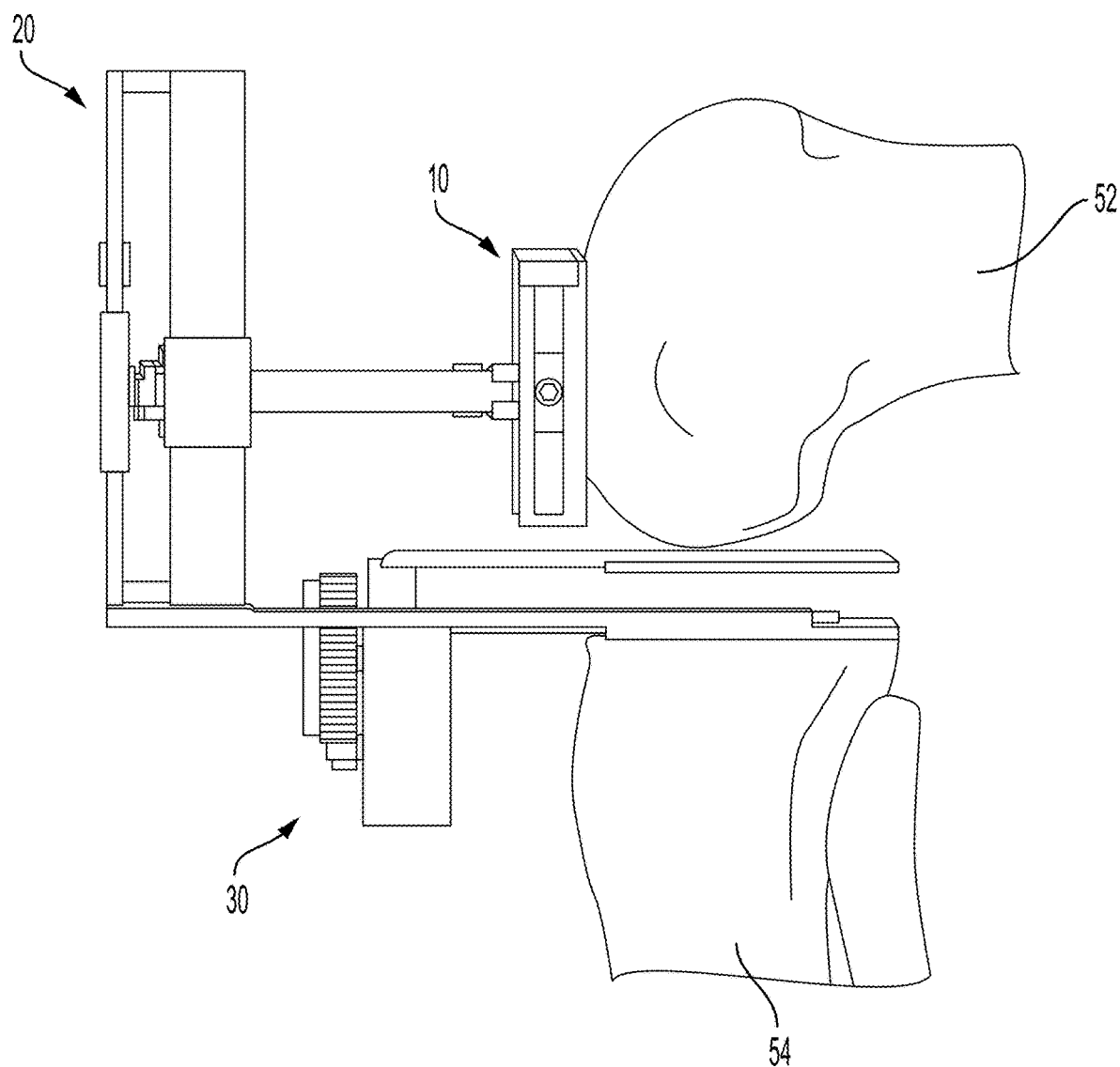
FIG. 1B is a schematic diagram for the device in FIG. 1A together with a femur and a tibia.

FIG. 1A shows one exemplary embodiment of a device 100 for assisting femoral component placement in total knee arthroplasty. FIG. 1B shows the device 100 being used with a femur 52 and a tibia 54.

Referring to FIGS. 1A and 1B, the device 100 may include a portion or all of the following components: a femoral block 10, a mechanical graph 20, and/or a distractor 30. The femoral block 10 may serve as a rigid point attachment to a distal end of the femur 52. The mechanical graph 20 may link to the femoral block 10. The distractor 30 may provide a constant distracting force between the femur 52 and the tibia 54.

Figure 2A:
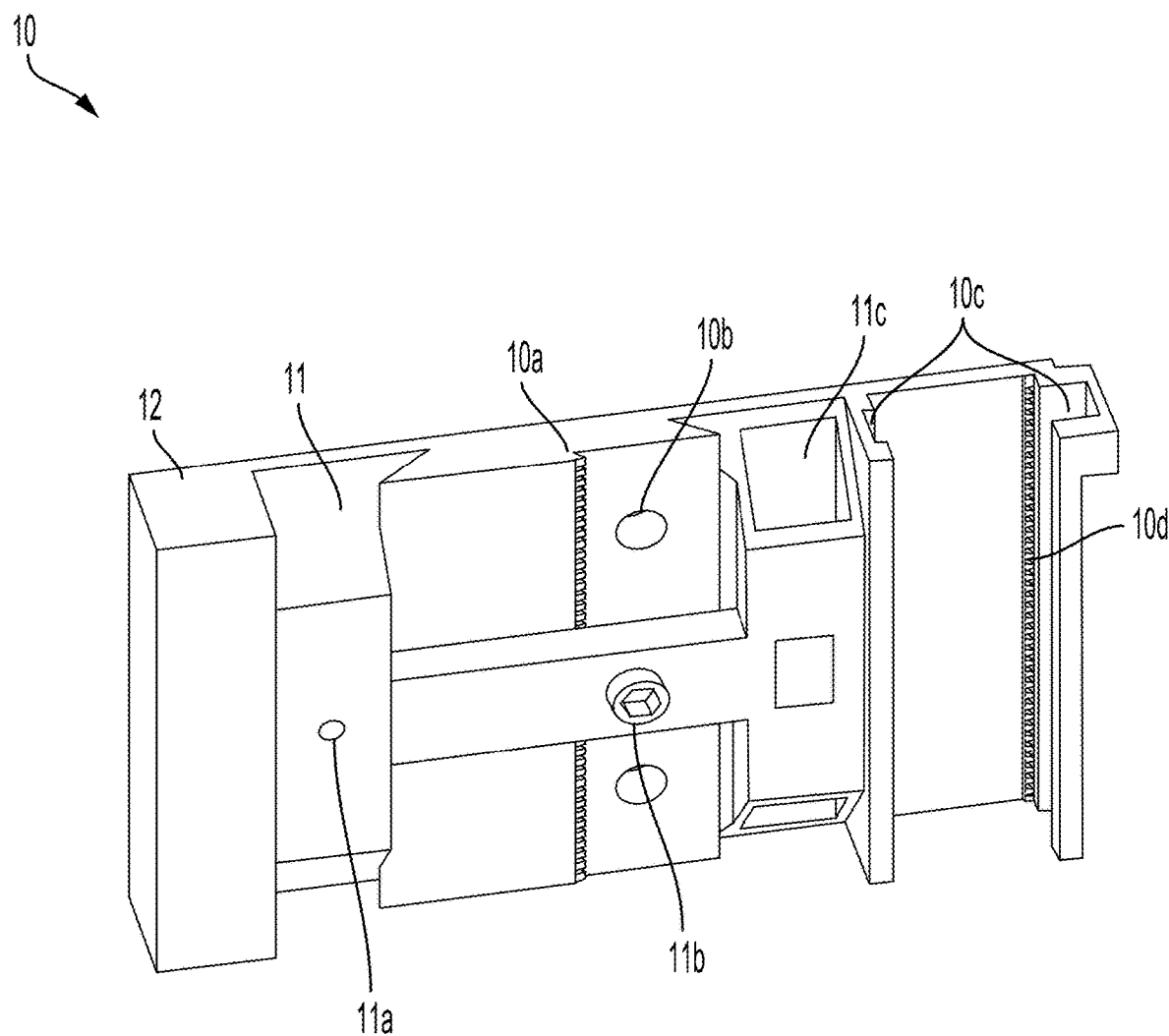
FIGS. 2A-2C are schematic diagrams of one embodiment of a femoral block.
Figure 2B:
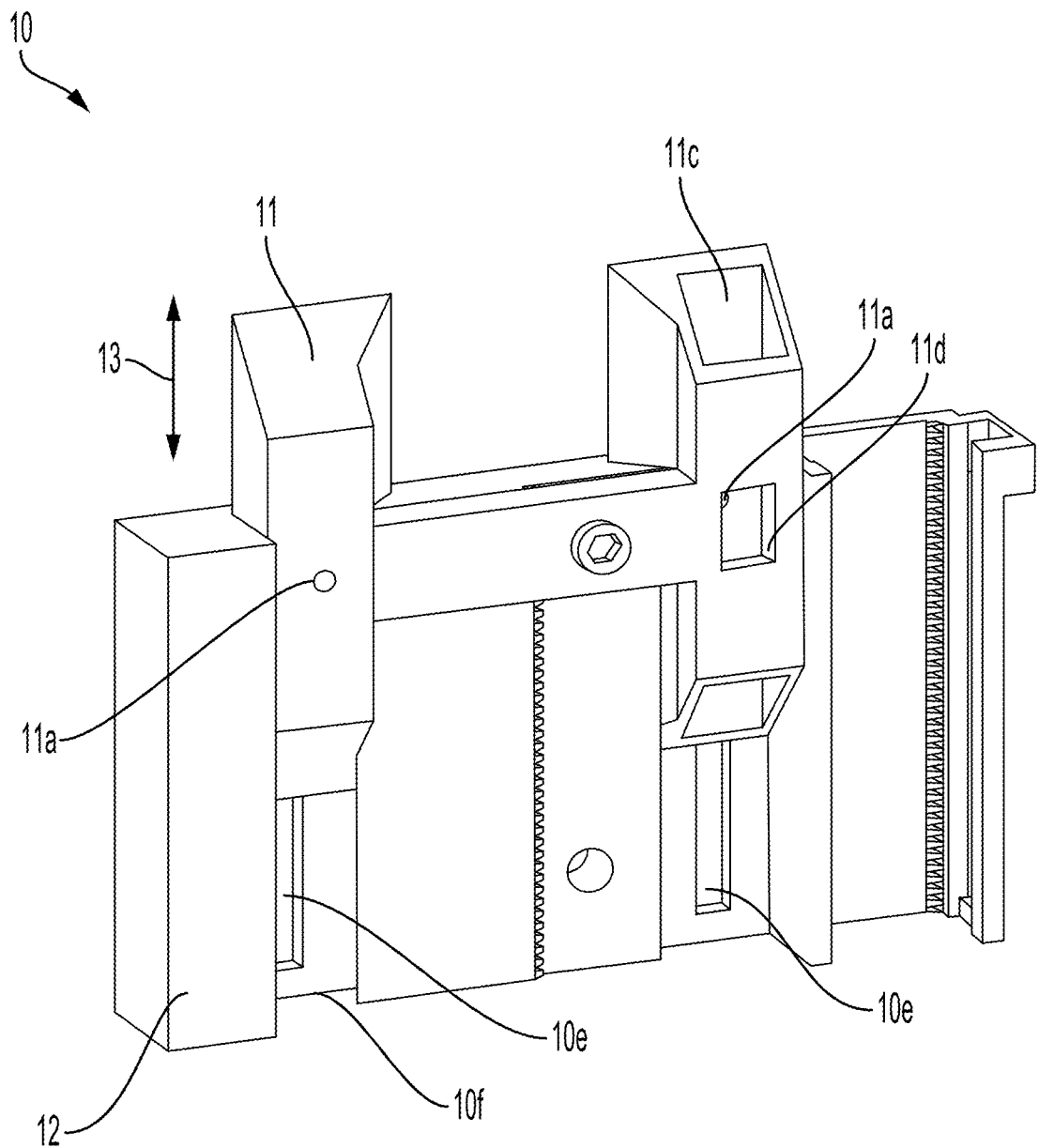
Figure 2C:
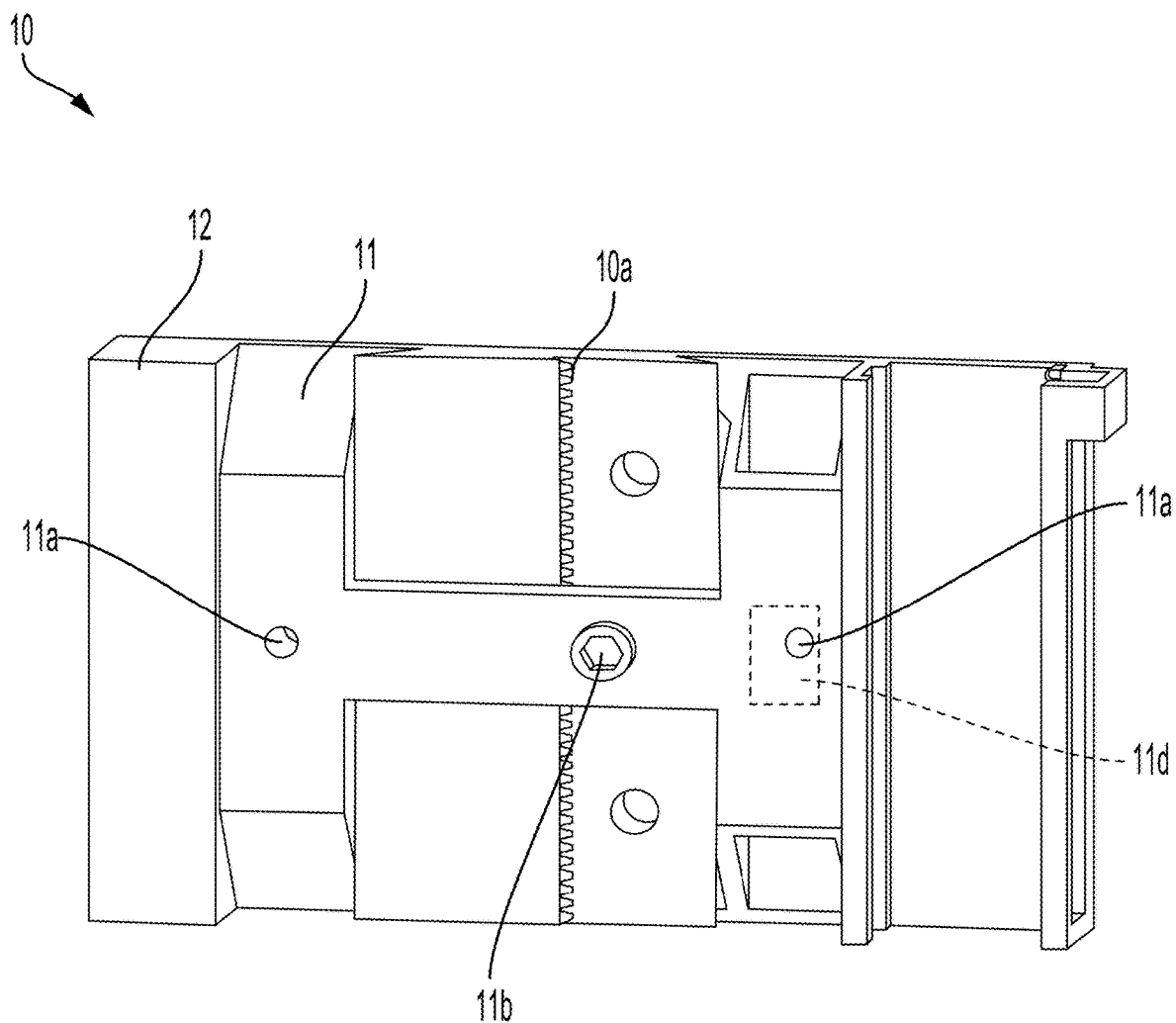

FIGS. 2A-2C show one exemplary embodiment of a femoral block 10. The femoral block 10 may serve as a rigid point of attachment to a distal femur. The femoral block 10 may include a main body 12, and a sliding member 11.

The main body 12 may be secured to the distal femur via a set of fasteners inserted through a set of holes 10b in the main body. For example but not limited to, the set of fasteners may include screws, nails, or bolts.

The main body 12 may include a set of grooves 10c at a right side of the main body. The set of grooves 10c may accept a portion of the mechanical graph, for example, a link 22a of a proximal end of the mechanical graph in FIG. 3C. The main body 12 may include a rack 10d along one of the set of grooves. The rack and pinion mechanism of the rack 10d and a pinion gear 22g in FIG. 3C enable a fine adjustment of the attachment of the mechanical graph to the femoral block.

Referring to FIGS. 2B and 2C, the sliding member 11 is slidable relative to the main body 12. In particular, the sliding member 11 may slide in another set of grooves 10f in the main body along a direction 13. The sliding member 11 may be configured to adjust an anterior-posterior position of a set of reference holes 11a. Pegs of a standard 4:1 femoral cutting guide may fit into holes drilled through the set of reference holes 11a in the femoral slide. As shown in FIG. 2B, the set of reference holes 11a are aligned with a set of slots 10e in the main body 12. The set of reference holes 11a may be drilled in any displacement of the slide with the set of slots 10e in the main body 12. A rack 10a and pinion configuration may provide fine sliding adjustments of the sliding member 11. A pinion gear may be coupled with a screw 11b, so that turning the screw 11b may lead to a sliding motion of the sliding member 11 relative to the main body 12. For example but not limited to, the screw 11b may be a standard 3.5 hex screwdriver. The sliding member 11 may include a slot 11c configured to accept a femoral sizer. In one implementation, a distance from the reference holes 11a and the anterior aspect of the femur is measured through an anterior stylus (not pictured) that is read through the square opening 11d above the reference hole 11a on the right. This embodiment allows for accurate sizing of the femoral component based on the position of the drill holes for a standard 4:1 femoral cutting block.

Figure 3A:
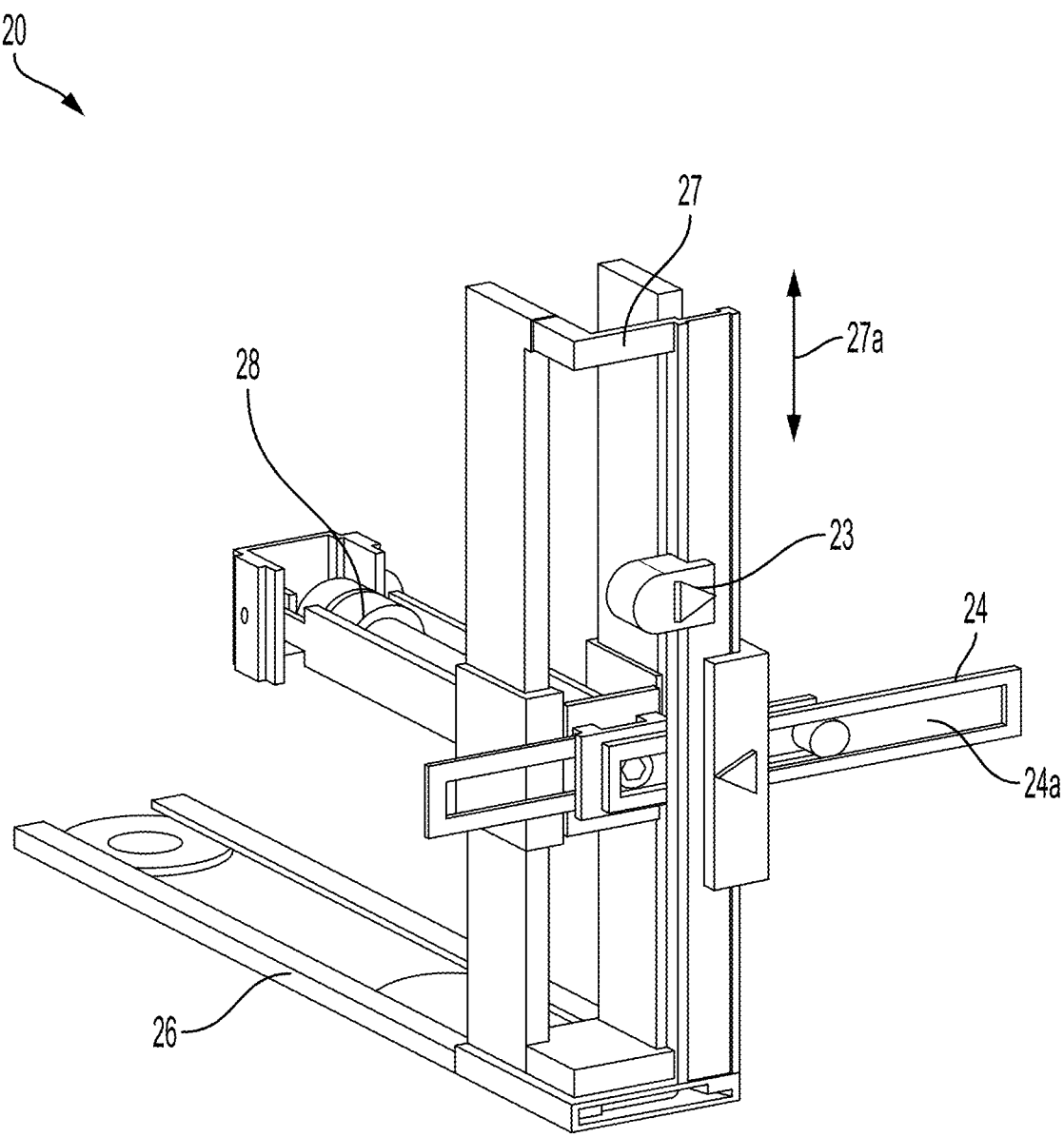
Figure 3B:
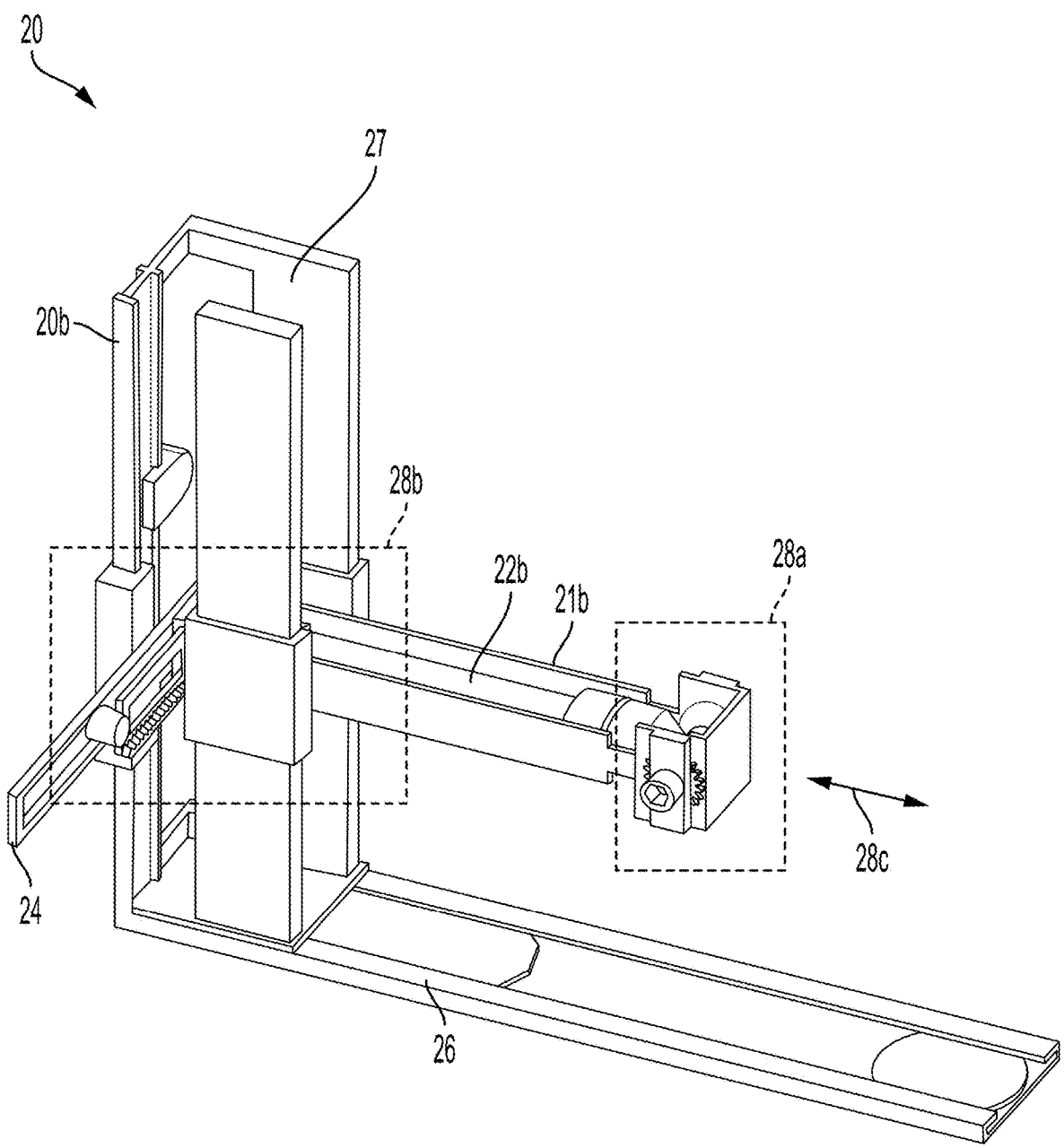
Figure 3C:
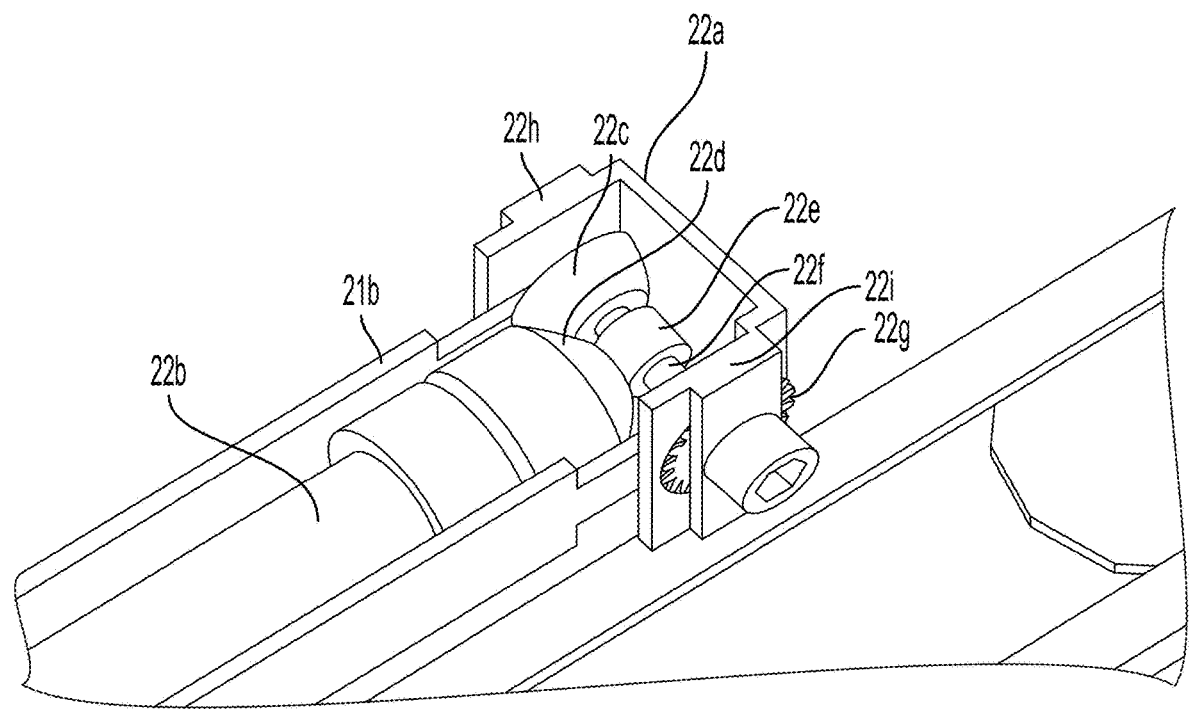

FIGS. 3A-3C show one exemplary embodiment of a mechanical graph 20. The mechanical graph 20 may represent the vertical displacement of a point on the femur that is adjustable by the medical care provider. One of the goals for the mechanical graph may be to find the isometric point of the femur during flexion, which is the point in space that maintains a single vertical displacement in relation to the tibia in all degrees of flexion. The mechanical graph 20 may link to the femur in order to track vertical displacement via the femoral block 10. The mechanical graph 20 may include a portion or all of the following components: a base 26, a tower 27, a vertical marker 23, a vertical reference 24, and/or a drive shaft assembly 28.

Referring to FIGS. 3A and 3B, the drive shaft assembly 28 may include a portion or all of the following: a drive shaft 22b, one or more drive shaft arms 21b, a proximal portion 28a, and/or a distal portion 28b. The drive shaft 22b and the one or more drive shaft arms 21b may be between the distal portion 28b and the proximal portion 28a. The distal portion 28b of the drive shaft assembly may be slidable on the tower along a longitudinal axis 27a of the tower. The distal portion 28b of the drive shaft assembly may be operatively connected to the vertical reference 24, the proximal portion 28a of the drive shaft assembly may be operatively connected to the femoral block 10 in FIG. 1A. The drive shaft assembly may have a longitudinal axis 28c.

The tower 27 may be fixedly connected to the base 26. The longitudinal axis 27a of the tower may be substantially perpendicular to a plane of the base 26. The tower 27 may include a first column 20b. The vertical marker 23 may be slidable along the first column 20b. The vertical reference 24 may be slidable along the first column 20b. The vertical reference may include a slot 24a.

Referring to FIGS. 1A and 3C, the proximal portion of the mechanical graph slides into the femoral block superiorly. The proximal portion of the drive shaft assembly may include a link 22a rotatably connected with a proximal end of the drive shaft arms 21b, a stationary gear 22c fixedly connected to the link, a mobile gear 22d fixedly connected to the drive shaft 22b.

Referring to FIG. 3C, the link 22a may include a set of protruding portions (22h and 22i), which operatively engages with the set of grooves 10c of the femoral block in FIG. 2A. The link 22a of the drive shaft assembly may slide in the grooves 10c of the femoral block via a rack and pinion mechanism, wherein the link 22a includes the pinion gear 22g and the femoral block includes the rack 10d in FIG. 2A.

The link 22a is connected to the stationary gear 22c. This stationary gear 22c may not rotate in relation to the link 22a and therefore represents the flexion angle of the femur. The stationary gear 22c articulates with the mobile gear 22d. The mobile gear 22d may be fixedly connected to the drive shaft 22b. The mobile gear 22d rotates around a fixed axis 22f of the stationary gear via a connection 22e. The proximal portion may be able to be adjusted in relation to a main body of the femoral block through a rack and pinion mechanism, with the pinion gear 22g mounted within the main housing of the proximal mechanical graph.

Figure 3D:
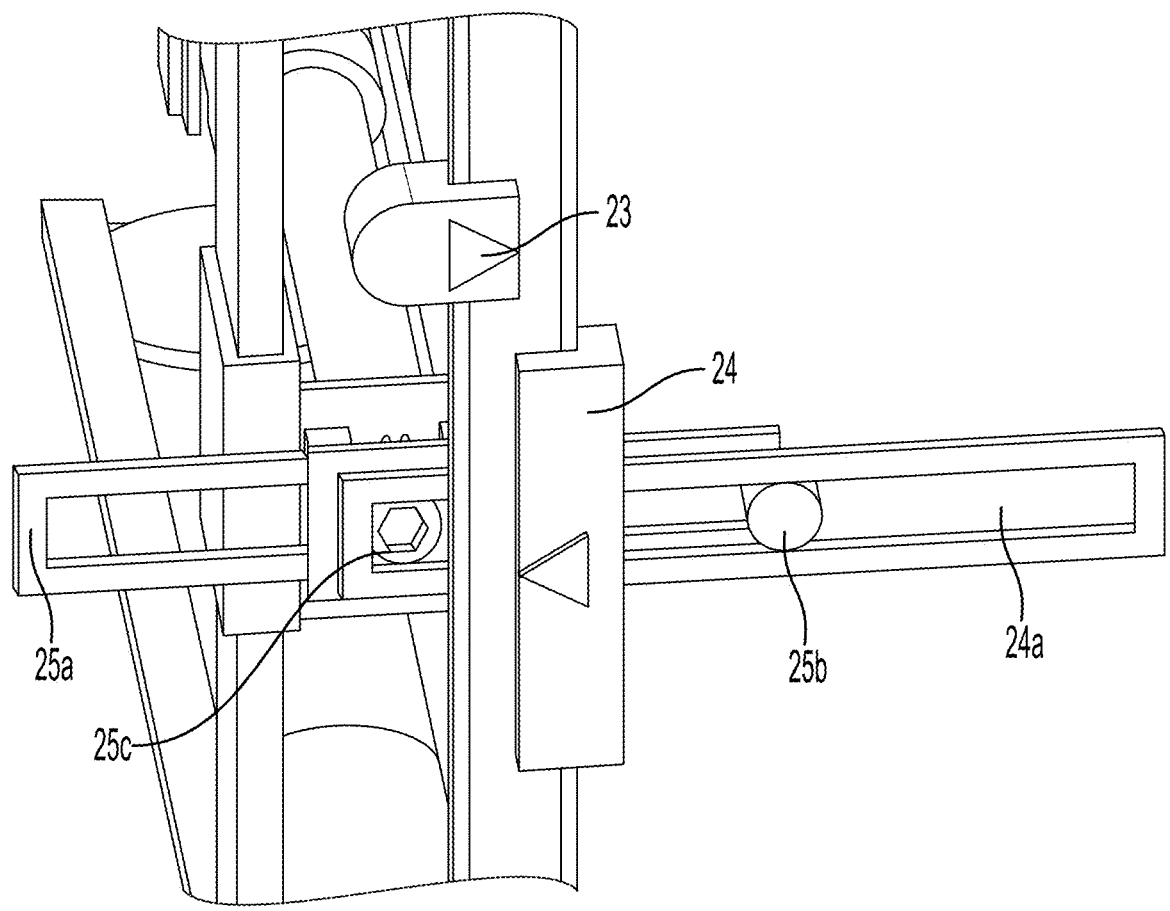
Figure 3E:
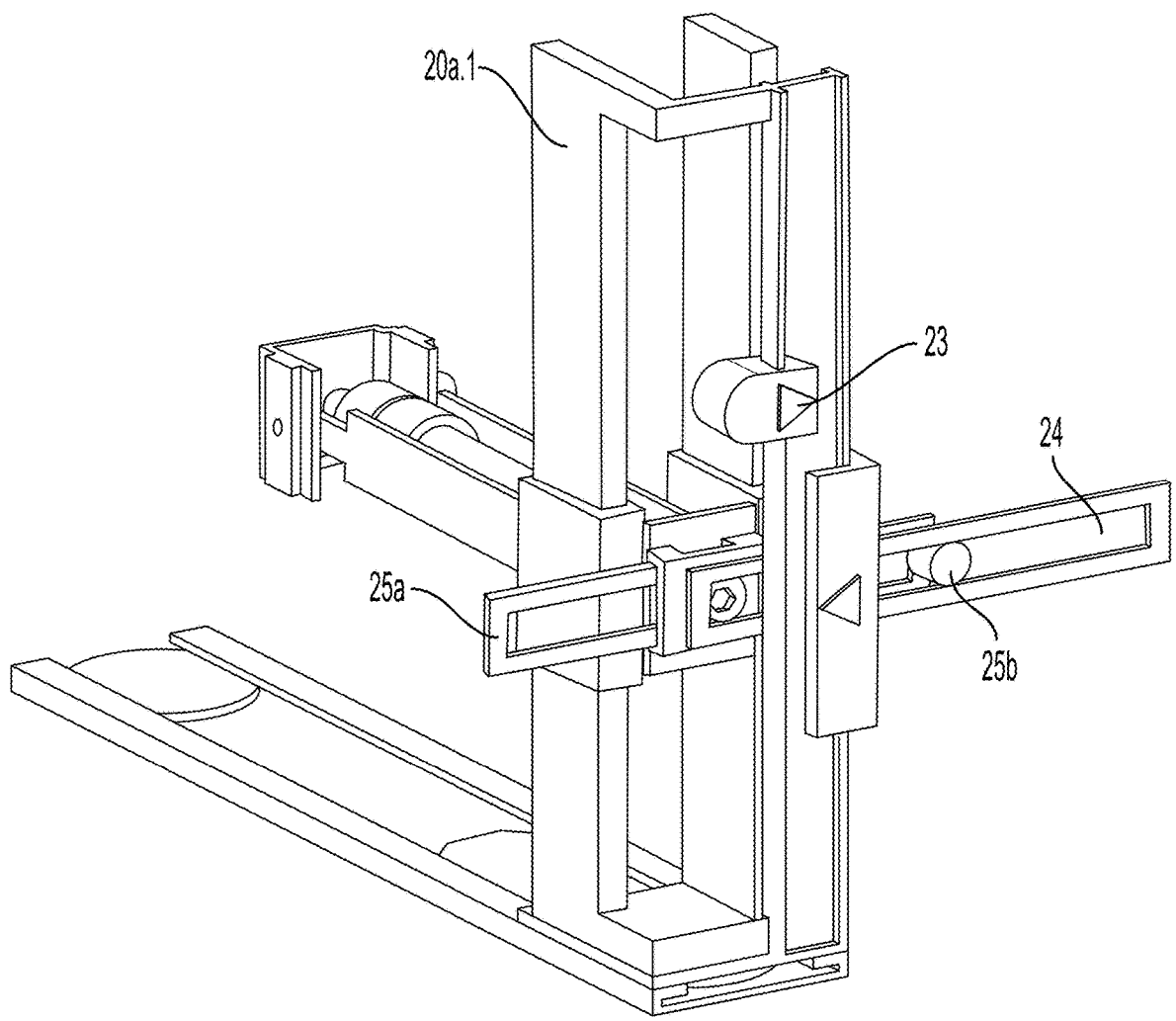
Figure 3F:
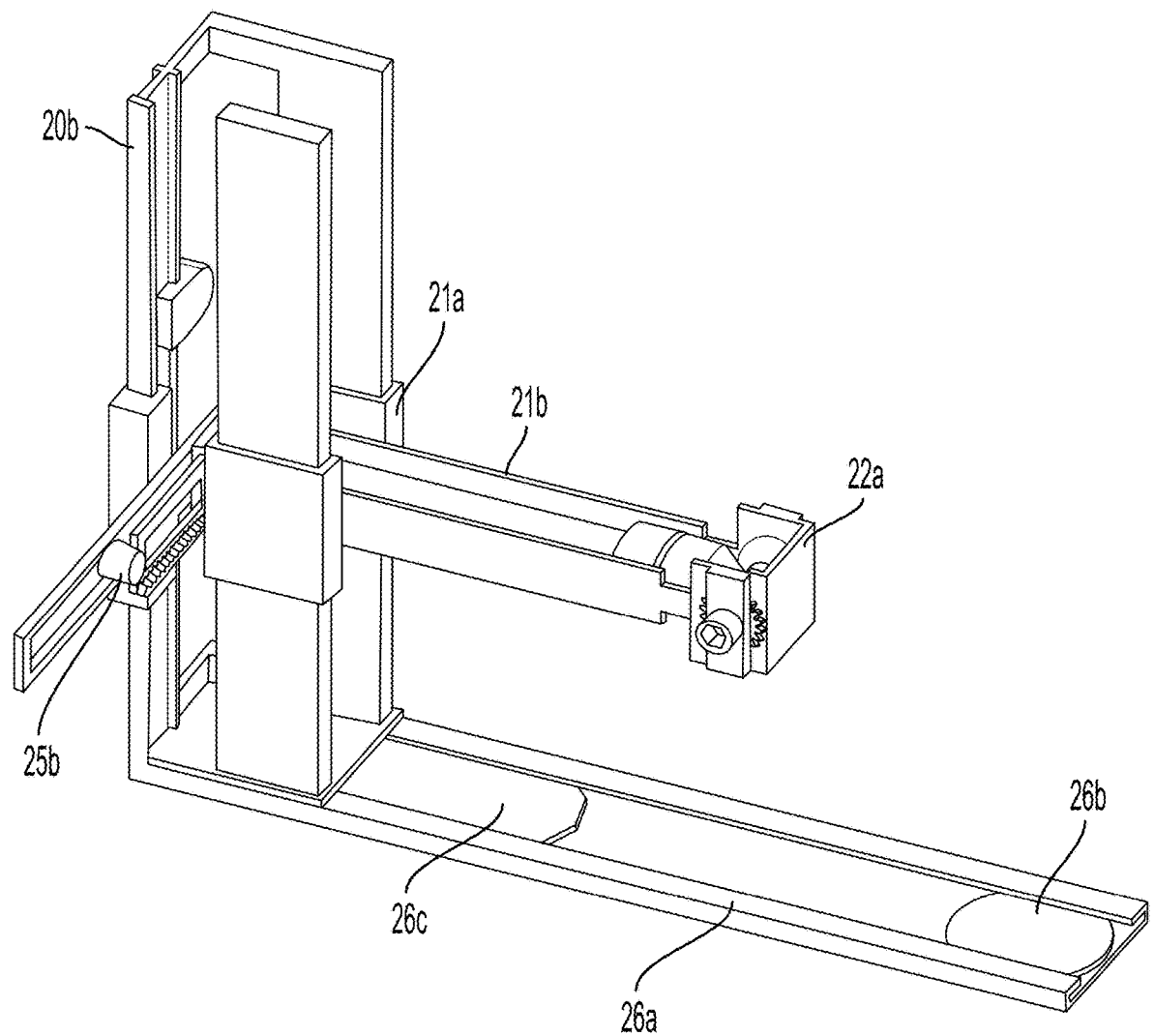

Referring to FIG. 3D-3F, the distal portion of the drive shaft assembly may include a portion or all of the following components: a distal baseplate 25c, a rotating arm 25a, a cylindrical extension 25b. The distal baseplate 25c may be disposed at a terminal of the distal portion. The rotating arm 25a may be operatively connected with the drive shaft 22b via a rack and pinion mechanism at the distal baseplate 25c. The cylindrical extension 25b may be disposed at an end of the rotating arm 25a, and the cylindrical extension 25b may be slidable in a slot 24a of the vertical reference 24.

The rotating arm 25a may be adjustable in term of its length via a rack and pinion mechanism mounted on the distal baseplate 25c. The rotating arm 25a may engage the vertical reference 24 via the cylindrical extension 25b. This connection may allow the vertical displacement of the adjustable length rotating arm to be tracked vertically. The vertical displacement of the vertical reference may be marked with the vertical marker 23.

The drive shaft assembly may be kept perpendicular to the tibia and free to slide vertically along the tower with a set of connectors 21a. The drive shaft assembly may be adjusted corresponding to changes in vertical femoral displacement via the connection of the drive shaft arms 21b, to the tower 27.

The entire mechanical graph may include a base 26 to support the mechanical graph. The base 26 may include a rigid "diving board" 26a that extends off a tibial plate. This ensures that the mechanical graph always measures from the plane of the tibia. Two degrees of freedom in that tibial plane are made possible by articulations of the diving board with the mechanical graph at the 22c baseplate, and connections with a tibial paddle via one or more connectors 22b.

As the femur flexes and extends, the stationary gear 22c and the mobile gear 22d may articulate at a 1:1 gear ratio, so that the drive shaft 22b of the mechanical graph is rotated along the longitudinal axis 28c at a 1:1 angular ratio compared to the flexion of the femur.

Figure 3G:
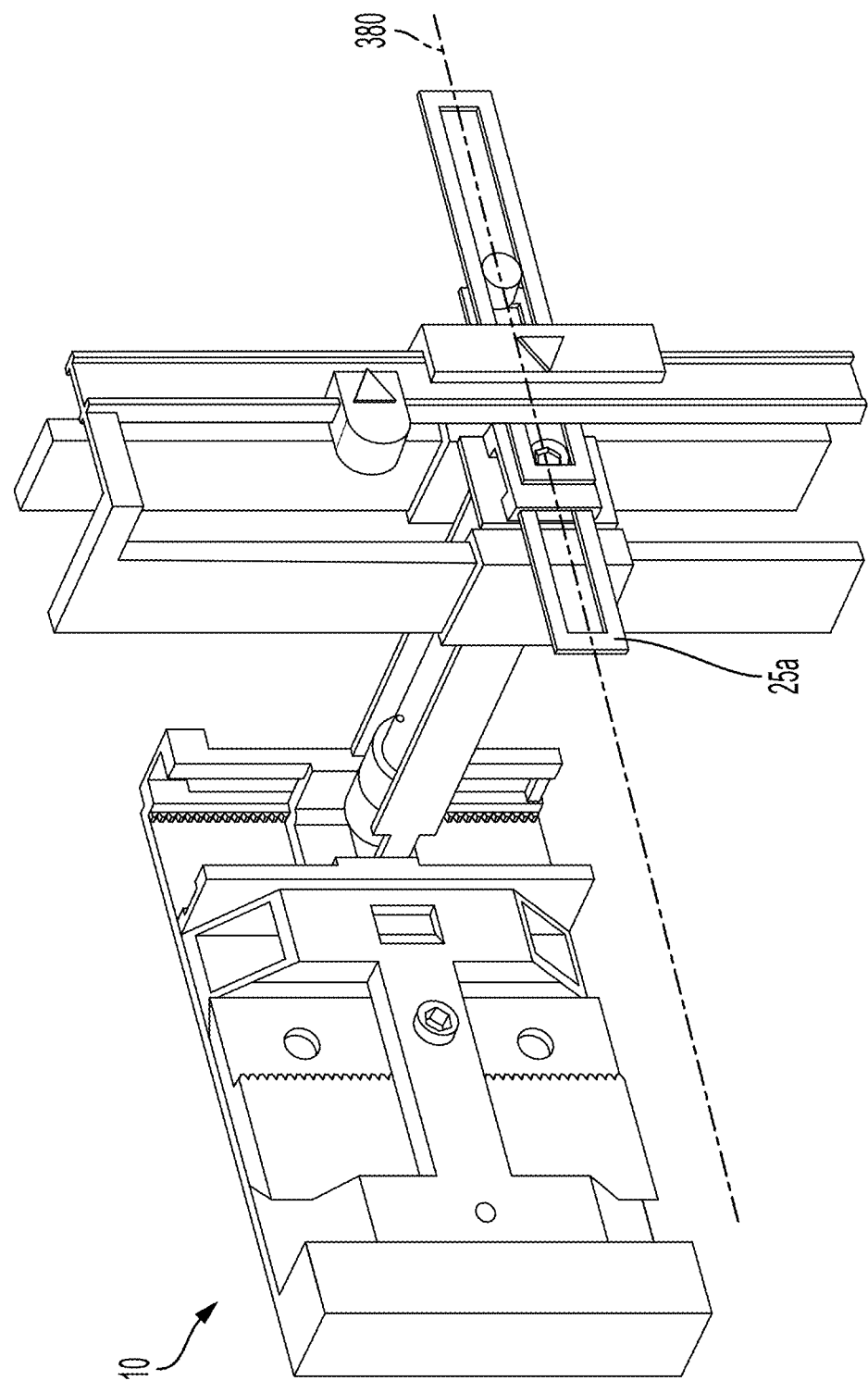
Figure 3H:
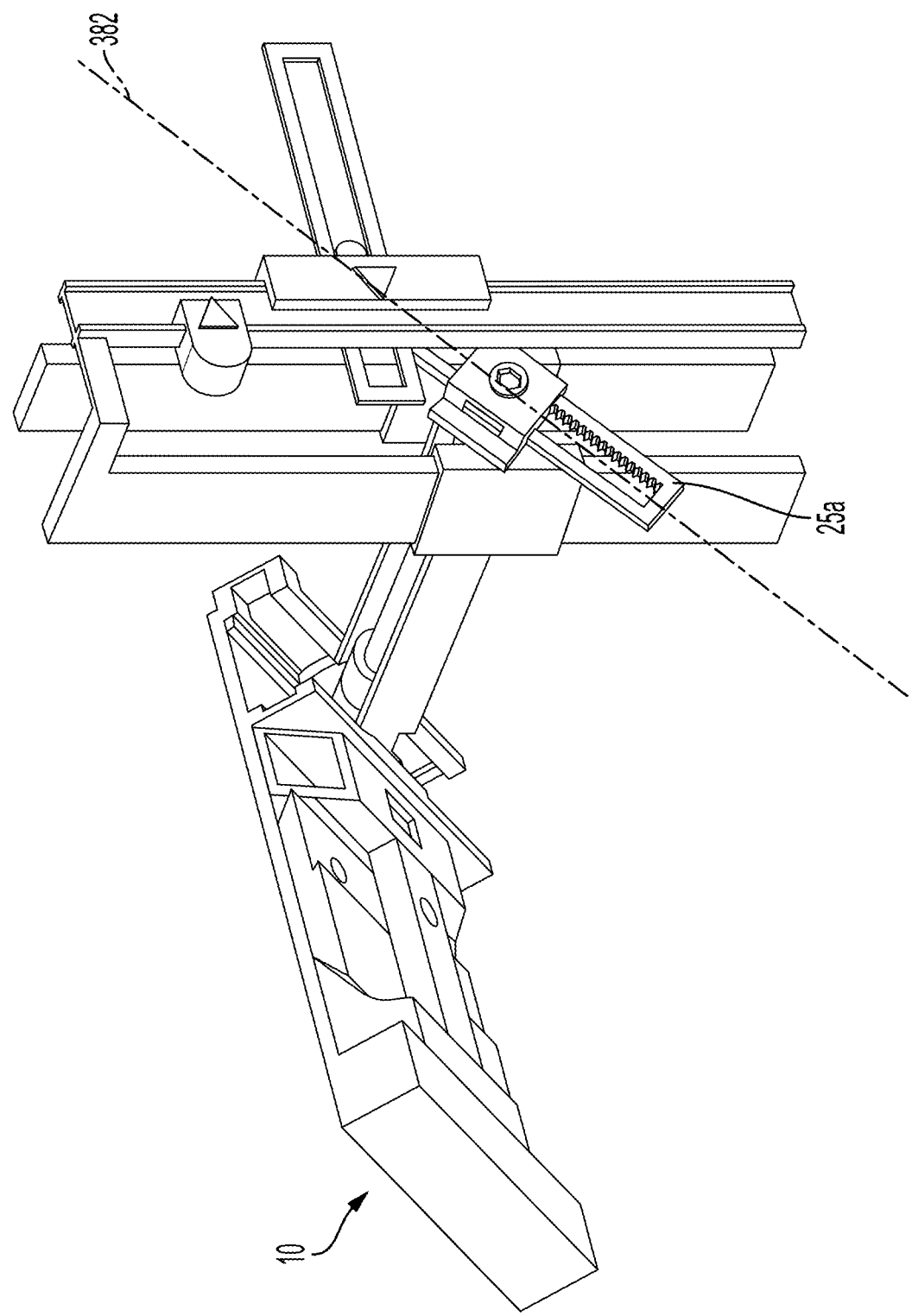
Figure 31:
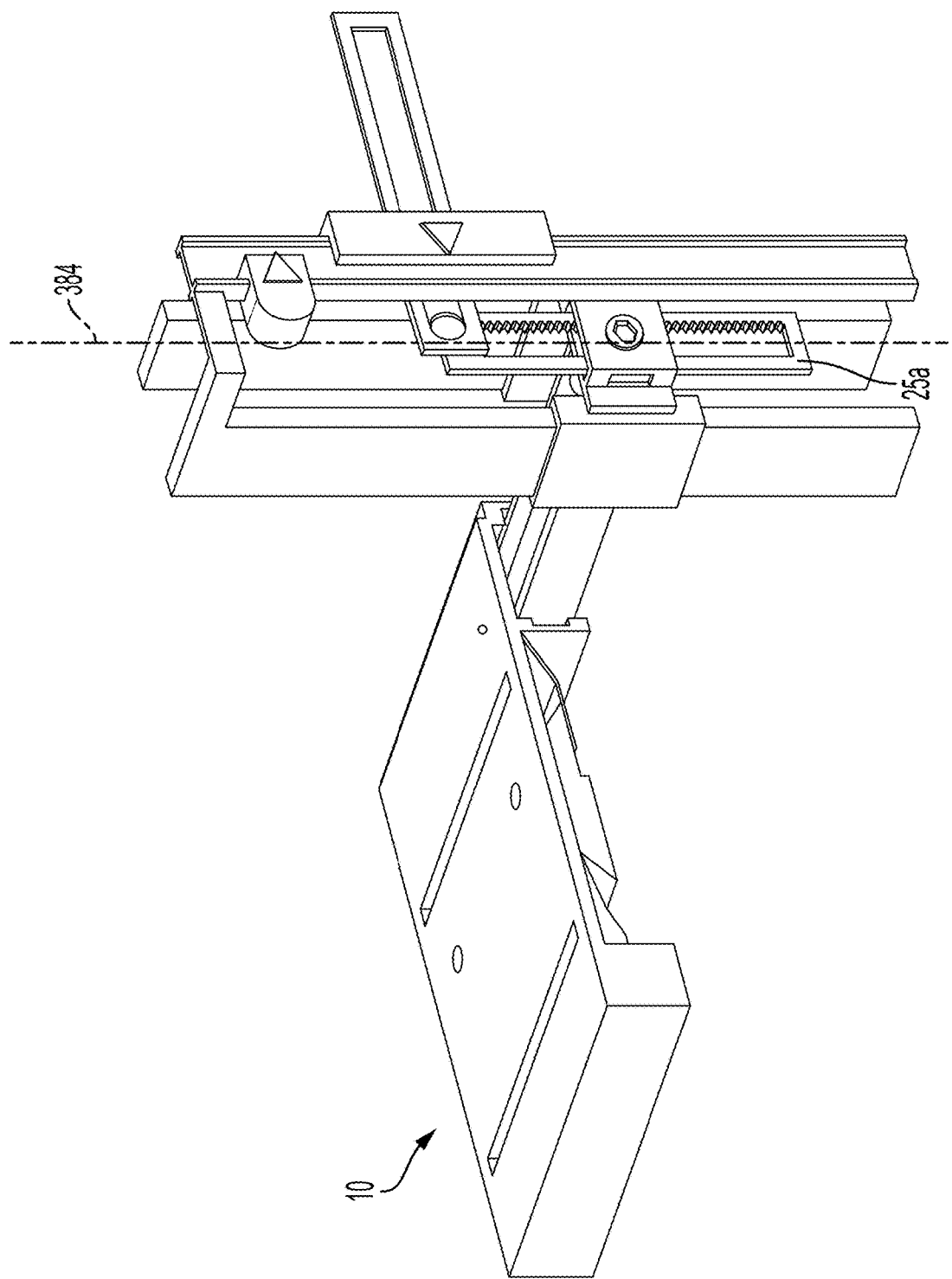

FIGS. 3G-3H show positions of the rotating arm when the femur flexes at various angles. For example, referring to FIG. 3G, the femur fixedly connected with a femoral block 10 is at 90 degrees of flexion, the rotating arm 25a may display a 90-degree orientation 380. Referring to FIG. 3H, the femur fixedly connected with a femoral block 10 is at 45 degrees of flexion, the rotating arm 25a may display a 45-degree orientation 382. Referring to FIG. 3I, the femur fixedly connected with a femoral block 10 is at 0 degree of flexion, full extension, the rotating arm 25a may display a 0-degree orientation 384. At flexion angles above 90 degrees, an indicator may be below horizontal, and the vertical reference 24 will still represent the correct vertical placement of the femoral point. Through systematically trialing different points in space, the medical care provider may be able to identify an isometric point of the femur as the point in space that maintains a single vertical displacement.

In another embodiment of the device, a microprocessor and simple display calculate and display the same information may be used to replace a portion of the function of the mechanical graph.

Once this isometric point is identified, the present disclosure may facilitate the placement of pins for a distal femur cutting block with holes and/or drill holes for a 4:1 femoral cutting block with pegs through guide holes provided by the slide of the femoral block that is adjusted during trialing of different points in space. The medical care provider has the option of adjusting lateral cutting block pins in standard fashion based on mechanical component alignment for the distal femoral cut and anatomic femoral rotation for the anterior, posterior, and chamfer femoral cuts. Once cuts are made and trial components are placed, a tensioning portion of the device may be once again placed in the knee as a way to measure the femoral-tibial gap at constant distraction force at all degrees of flexion to ensure perfect sagittal balance has been achieved and as a way to measure and select optimum final polyethylene insert thickness.

FIGS. 4A-4D show one exemplary embodiment of a distractor 30. The distractor may serve to provide a constant force to distracting a femur and a tibia. For example but not limited to, the generation of constant force may be achieved through the use of a coiled constant force spring. This coiled constant force spring may be mounted in a housing that allows it to engage a geared articulation between a femoral and tibial paddle, thereby creating a constant distraction force between the femur and tibia force at a variable distraction distance. This spring housing may be fashioned so that it is easily removed from the main structure of the device and replaced with a housed spring of a greater or lesser distraction force depending on the anatomy of a patient.

The distractor 30 may include a portion or all of the following components: a main body 33, a tibial paddle 32, one or more femoral paddles (31a.1 and 31a.2), a spring housing 34a, a coiled constant force spring, an inner gear 34b, a primary rack 36a, and/or a winding gear 35.

The tibial paddle 32 may be fixedly connected to the main body 33. The tibial paddle may include a bottom surface 32c, which is configured to push against a top of a tibia as shown in FIG. 1B. each of the one or more femoral paddles may include a top surface 31c which is configured to push against a bottom of a femur as shown in FIG. 1B. The top surface 31c and the bottom surface 32c may be substantially parallel to each other. Here, the "substantially parallel" may refer to two surface are parallel within 10 degrees.

The spring housing 34a may be fixed on the main body 33. The coiled constant force spring may be disposed in the spring housing 34a. The spring housing 34a may be attached to an outer end of the coiled constant force spring, and the coiled constant force spring is configured to apply the constant distracting force on the one or more femoral paddles. The inner gear 34b may be attached to an inner end of the coiled constant force spring. The winding gear 35 may be disposed on the main body, and may be operatively connected to the spring housing. The winding gear 35 may include a ratchet mechanism so that it only be allowed to rotate in one direction, for example, a clockwise direction. When the winding gear is rotated, the winding gear may wind the coiled constant force spring to store mechanical energy in the coiled constant force spring.

In some embodiments, the one or more femoral paddles may include two femoral paddles: a first femoral paddle and a second femoral paddle. The distractor 30 may further include a portion or all of the following components: a first rack 31b.1 fixedly connected to the first femoral paddle 31a.1, a second rack 31b.2 fixedly connected to the second femoral paddle 31a.2, one or more internal gears 37a.1 operatively connected with the first rack and the second rack (31b.1 and 31b.2). The primary rack 36a may be fixedly connected to the one or more femoral paddles (31a.1 and 31a.2). In particular, in one example shown in FIG. 4C, primary rack 36a may be fixedly connected to the first femoral paddle 31a.1. The primary rack 36a may be operatively connected with the inner gear 34b, and the rotation of the inner gear 34b configured to slide the first femoral paddle 31a.1 via a rack and pinion mechanism.

In some embodiments, a constant-force distractor may include the one or more femoral paddles (31a.1 and 31a.2) and the tibial paddle 32. The tibial and femoral paddles may be linked by a set of gears. The tibial paddle may be an integral part with the main body 33 of the distractor. The constant distracting force may be generated by a coiled constant force spring that is mounted in the spring housing 34a. An inner aspect of the coiled spring may attach to the inner gear 34b. This configuration allows the entire force of the spring to be transmitted to the one or more femoral paddles via engaging the primary rack 36a as a rack and pinion mechanism. The spring mechanism may be wound by the winding gear 35. The winding gear 35 may engage with the outside of the spring housing, and may be only allowed to turn clockwise, so that the stored energy in the coiled constant force spring may be maintained by the winding gear 35. The distraction of the femoral paddles may be transmitted through the vertical displacement of internal gears 37a.1.

Figure 4A:
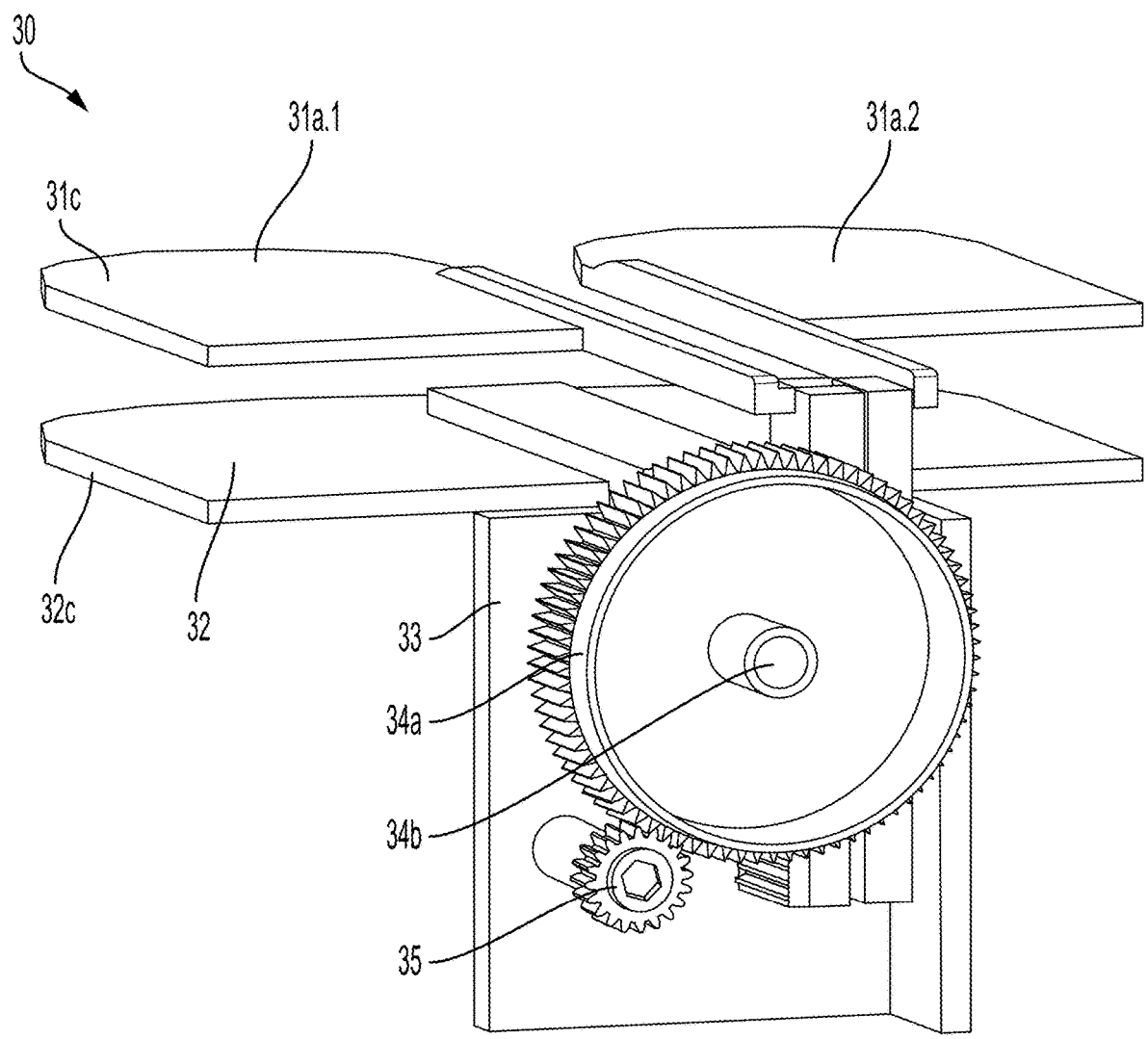
FIGS. 4A-4D are schematic diagrams of one embodiment of a distractor.
Figure 4B:
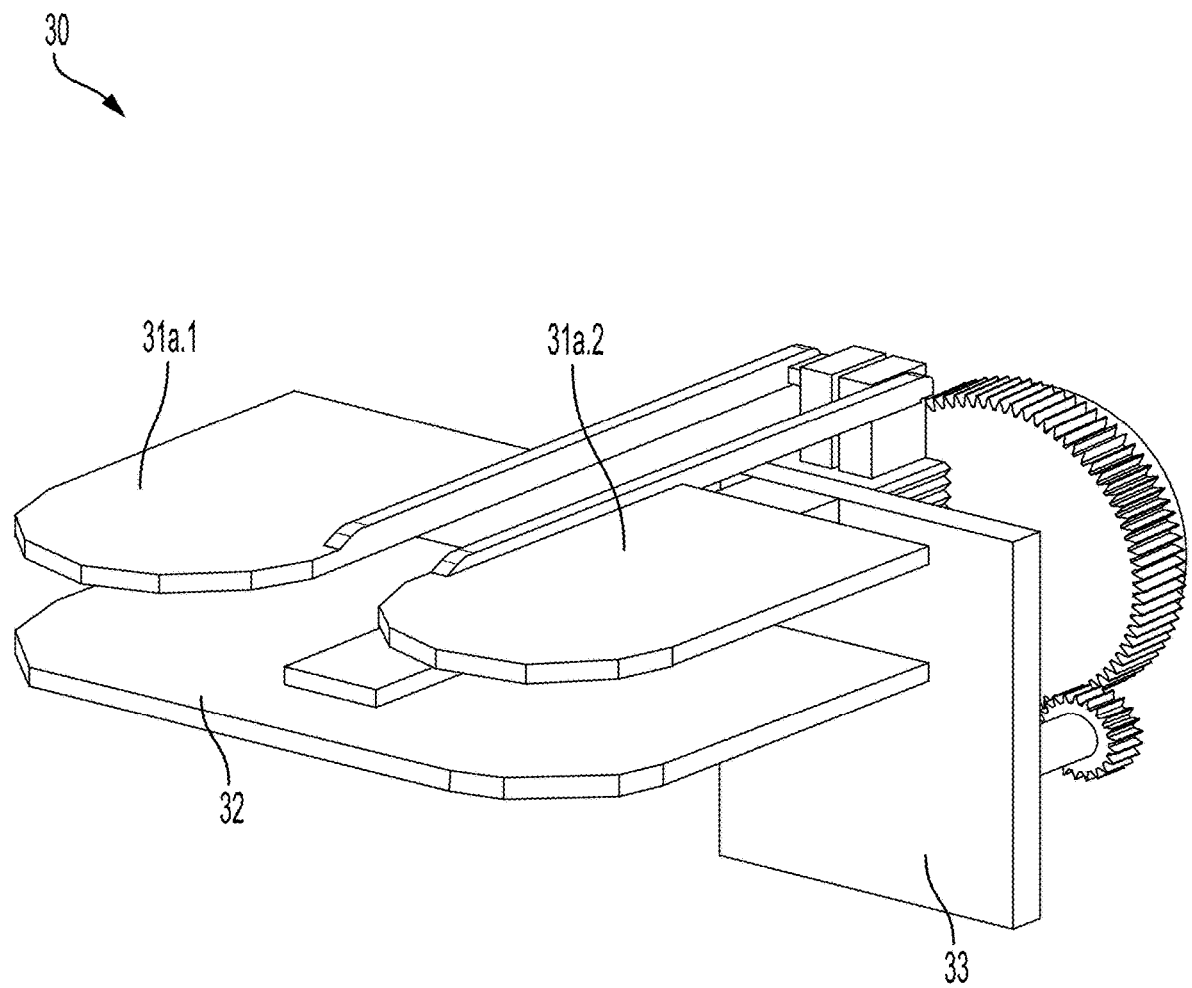
Figure 4C:
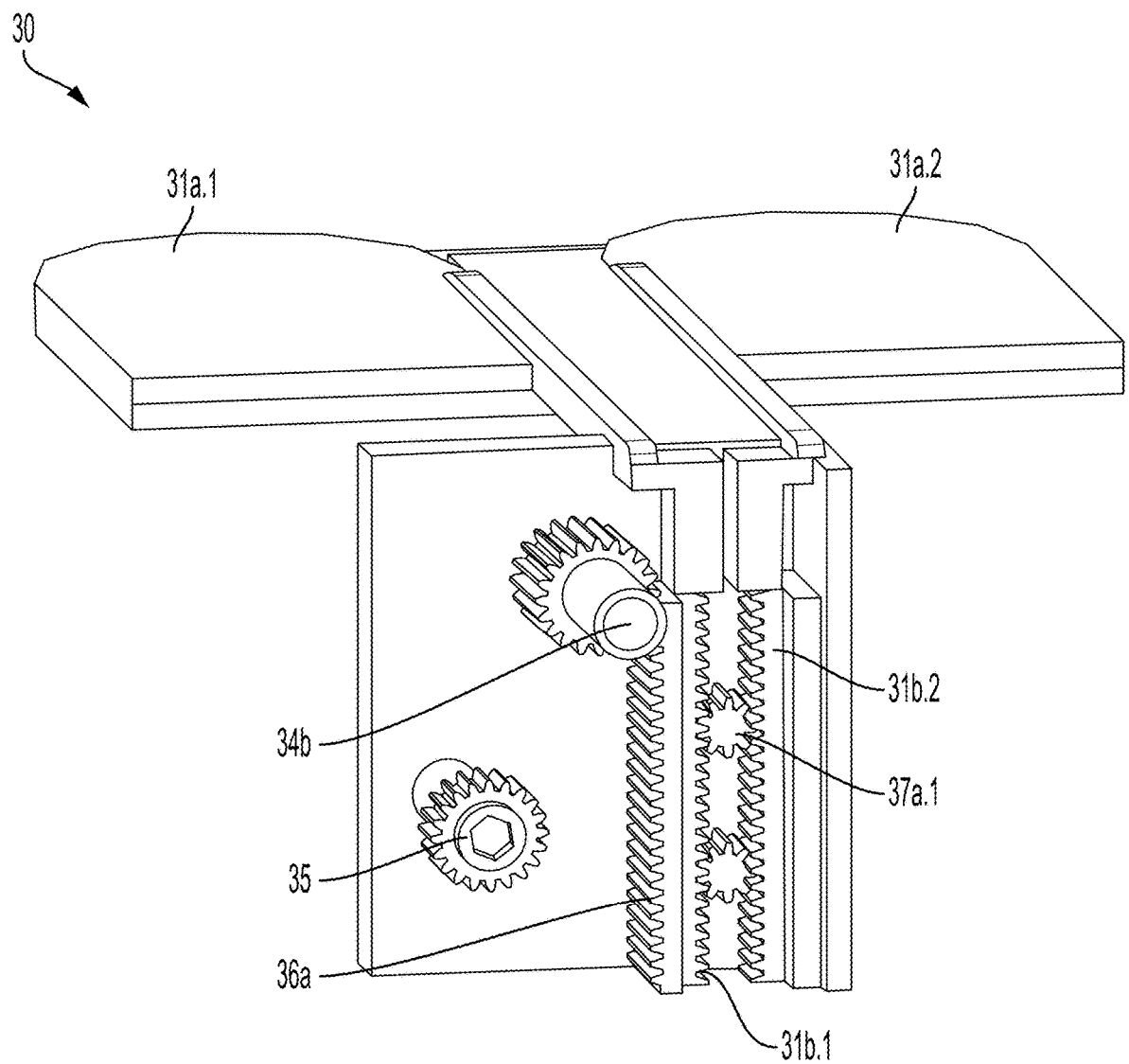
Figure 4D:
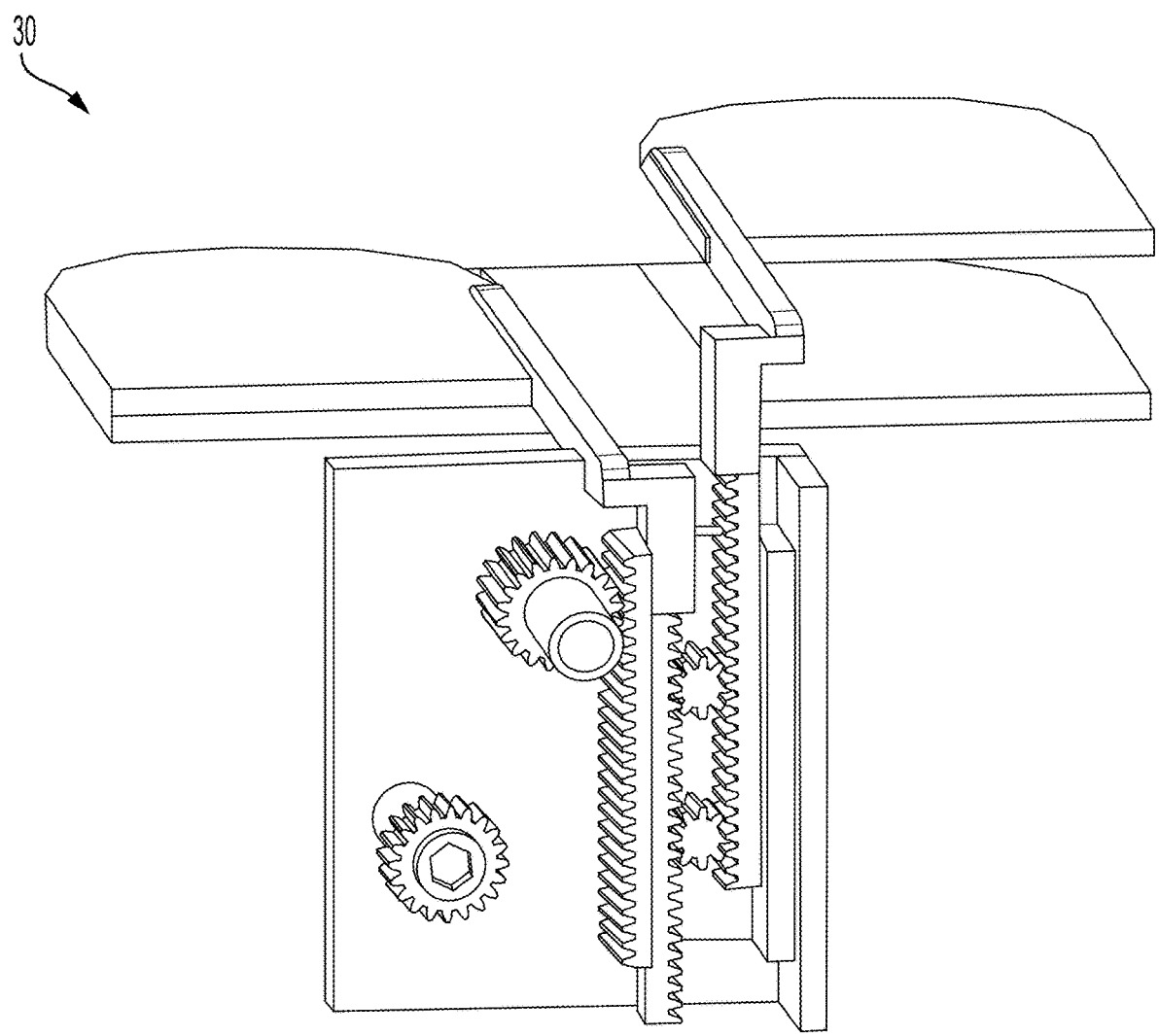

Referring to FIG. 4D, while these internal gears are distracted vertically, the first and second femoral paddles may be allowed to occupy a different, although linked, vertical displacement. Therefore, force to each femoral condyle remains equal and constant throughout any vertical displacement. In one implementation, the first and second femoral paddles may be medial and lateral femoral paddles, respectively.

Through the descriptions of the preceding embodiments, persons skilled in the art may understand that the device, system, and/or method according to the foregoing embodiments may be implemented by hardware only or by software and a necessary universal hardware platform. In some cases, using software and a necessary universal hardware platform are preferred.

While the particular disclosure has been described with reference to illustrative embodiments, this description is not meant to be limiting. Various modifications of the illustrative embodiments and additional embodiments of the invention will be apparent to one of ordinary skill in the art from this description. Those skilled in the art will readily recognize that these and various other modifications can be made to the exemplary embodiments, illustrated and described herein, without departing from the spirit and scope of the present invention. It is therefore contemplated that the appended claims will cover any such modifications and alternative embodiments. Certain proportions within the illustrations may be exaggerated, while other proportions may be minimized. Accordingly, the disclosure and the figures are to be regarded as illustrative rather than restrictive.

What is claimed is:

1. A device for assisting femoral component placement in total knee arthroplasty, the device comprising:
    a distractor configured to provide a constant distracting force, wherein the distractor comprises:
        a main body of the distractor,
        a tibial paddle fixedly connected to the main body, the tibial paddle configured to engage a top of a tibia,
        at least one femoral paddle configured to push against a bottom of a femur,
        a spring housing fixed on the main body of the distractor, and
        a coiled constant force spring disposed in the spring housing, the spring housing attached to an outer end of the coiled constant force spring, the coiled constant force spring configured to apply the constant distracting force on the at least one femoral paddle,
    wherein the distractor further comprises:
        an inner gear attached to an inner end of the coiled constant force spring; and
        a primary rack fixedly connected to one of the at least one femoral paddle, the primary rack operatively connected with the inner gear, a rotation of the inner gear configured to slide the one of the at least one femoral paddle.

2. The device according to claim 1, wherein the distractor further comprises:
    a winding gear disposed on the main body of the distractor, the winding gear operatively connected to the spring housing, the winding gear rotatable in one direction configured to wind the coiled constant force spring.

3. The device according to claim 1, wherein:
    the at least one femoral paddle comprises a first femoral paddle and a second femoral paddle; and
    the distractor further comprises:
        a first rack fixedly connected to the first femoral paddle,
        a second rack fixedly connected to the second femoral paddle, and
        one or more internal gears operatively connected with the first rack and the second rack.

4. The device according to claim 1, wherein:
    a top surface of each of the at least one femoral paddle and a bottom surface of the tibial paddle are substantially parallel.

5. The device according to claim 1, the device further comprising:
    a mechanical graph configured to locate an isometric point of the femur, wherein the mechanical graph comprises:
        a base fixedly connected to the tibial paddle of the distractor,
        a tower fixedly connected to the base, a longitudinal axis of the tower being substantially perpendicular to a plane of the base, the tower comprising a first column,
        a vertical marker slidable along the first column,
        a vertical reference slidable along the first column, the vertical reference comprising a slot, and
        a drive shaft assembly comprising a shaft and at least one shaft arm disposed between a distal portion and a proximal portion, the distal portion of the drive shaft assembly slidable along the tower, the distal portion of the drive shaft assembly operatively connected to the vertical reference, the proximal portion of the drive shaft assembly operatively connected to a femoral block.

6. The device according to claim 5, wherein the distal portion of the drive shaft assembly comprises:
    a distal baseplate disposed at a terminal of the distal portion;
    a rotating arm operatively connected with the shaft via a rack and pinion mechanism at the distal baseplate; and
    a cylindrical extension disposed at an end of the rotating arm, the cylindrical extension slidable in the slot of the vertical reference.

7. The device according to claim 1, wherein the proximal portion of the drive shaft assembly comprises:
    a link rotatably connected with a proximal end of the at least one shaft arm;
    a stationary gear fixedly connected to the link; and
    a mobile gear fixedly connected to the shaft, the mobile gear operatively engaged with the stationary gear.

8. The device according to claim 7, wherein:
    a gear ratio between the stationary gear and the mobile gear is 1:1.

9. The device according to claim 7, the device further comprising:
    a femoral block comprising:
        a main body of the femoral block comprising a set of holes configured for a set of fasteners to secure the femoral block to the femur, and
        a sliding member slidable relative to the main body, the sliding member comprising a gear operatively connected to a rack of the main body via a rack and pinion mechanism.

10. The device according to claim 9, wherein the sliding member comprises:
    a set of reference holes aligned with a set of slots in the main body; and
    a slot configured to receive a femoral sizer.

11. The device according to claim 9, wherein:
    the link of the drive shaft assembly comprising a set of protruding portions operatively engaging with a set of grooves of the femoral block; and
    the link of the drive shaft assembly configured to slide in the set of groove of the femoral block via a rack and pinion mechanism.

* * * * *